(12) United States Patent
Liu et al.

(10) Patent No.: US 7,435,545 B2
(45) Date of Patent: Oct. 14, 2008

(54) METHOD FOR SIZING POLYNUCLEOTIDES USING ELECTROPHORESIS WITH NON-DNA SIZE STANDARDS

(75) Inventors: Zhaowei Liu, Port Matilda, PA (US); Thomas E. Kane, State College, PA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 11/103,356

(22) Filed: Apr. 11, 2005

(65) Prior Publication Data

US 2006/0029949 A1 Feb. 9, 2006

Related U.S. Application Data

(63) Continuation-in-part of application No. PCT/US03/32146, filed on Oct. 10, 2003, and a continuation-in-part of application No. 10/425,746, filed on Apr. 30, 2003, now abandoned.

(60) Provisional application No. 60/608,700, filed on Sep. 10, 2004, provisional application No. 60/417,173, filed on Oct. 10, 2002, provisional application No. 60/376,565, filed on May 1, 2002.

(51) Int. Cl.
*C12Q 1/68* (2006.01)
(52) U.S. Cl. ...................................................... 435/6
(58) Field of Classification Search ........................ None
See application file for complete search history.

(56) References Cited

U.S. PATENT DOCUMENTS

| 5,162,514 | A | 11/1992 | Serwer et al. |
|---|---|---|---|
| 5,302,510 | A | 4/1994 | Klevan |
| 5,599,664 | A | 2/1997 | Schwartz |
| 5,641,665 | A | 6/1997 | Hobart et al. |
| 6,455,682 | B1 | 9/2002 | Barron |
| 6,723,515 | B2 | 4/2004 | Barron |
| 6,933,111 | B1 | 8/2005 | De Beucketeer et al. |

OTHER PUBLICATIONS

Basile et al., "Use of peptide nucleic acid probes for detecting DNA single-base mutations by capillary electrophoresis," Electrophoresis, 2002, vol. 23, pp. 926-929.*
Morell et al., Analysis of Starch Structure Using Fluorophore-Assisted Carbohydrate Electrophoresis, Electrophoresis 19:2603-2611, 1998.
"SNPlex™ Genotyping System 48-plex, Chemistry Guide", *Applied Biosystems*, 78 pages, (Jan. 2004).
World Intellectual Property Organization, International Search Report, PCT/US03/32146, Jul. 23, 2004, 4 pages.

* cited by examiner

*Primary Examiner*—Young J Kim
(74) *Attorney, Agent, or Firm*—McQuaide, Blasko, Fleming & Faulkner, Inc.

(57) ABSTRACT

According to a method of determining a size of a sample polynucleotide, a sample polynucleotide is subjected to electrophoresis in the presence of a fluorescent compound having a first fluorescence spectrum. Detection of light of the first fluorescence spectrum is indicative of the presence of the sample polynucleotide. One or more size standards are also subjected to electrophoresis, optionally in the presence of the sample polynucleotide. If more than one size standard is used, the different size standards typically have different mobilities. The size standards are generally essentially or completely free of polynucleotides. Migration coordinates, e.g., migration times, of the sample polynucleotide and size standard(s) are determined. A size of the sample polynucleotide can be determined using the migration coordinate of the sample polynucleotide and the migration coordinate(s) of the size standard(s).

18 Claims, 2 Drawing Sheets

METHOD FOR SIZING POLYNUCLEOTIDES USING ELECTROPHORESIS WITH NON-DNA SIZE STANDARDS

RELATED APPLICATIONS

The present application is a continuation-in-part of international application no. PCT/US2003/32146, filed Oct. 10, 2003 and a continuation-in-part of U.S. application Ser. No. 10/425,746, filed Apr. 30, 2003, now abandoned and claims the benefit of U.S. provisional application Nos. 60/417,173, filed Oct. 10, 2002, 60/376,565, filed May 1, 2002, and 60/608,700, filed Sep. 10, 2004. All of the foregoing applications are incorporated herein by reference in their entireties.

FIELD OF THE INVENTION

The present invention relates to a method for sizing polynucleotides by subjecting the polynucleotides to electrophoresis to obtain electrophoresis data and comparing the electrophoresis data to electrophoresis data obtained from one or more size standards.

BACKGROUND OF THE INVENTION

Sample polynucleotides may be subjected to electrophoresis in the presence of reference polynucleotides having a known size. Sample polynucleotides and reference polynucleotides having the same size generally exhibit the same mobility when subjected to electrophoresis. The size of the sample polynucleotides may be determined using migration times of the sample polynucleotides and of the reference polynucleotides.

Detection methods, such as fluorescence resulting from intercalating dyes, are typically sensitive to the presence of both the sample polynucleotides and the reference polynucleotides. Thus, electrophoresis data from a separation of sample polynucleotides and reference polynucleotides may include a sample polynucleotide peak that is obscured by a peak resulting from one of the reference polynucleotides.

SUMMARY OF THE INVENTION

A first aspect of the invention relates to a method for determining a size of a sample polynucleotide. A sample polynucleotide is subjected to electrophoresis in the presence of at least (1) a fluorescent compound having a first fluorescent spectrum, wherein detection of the fluorescence of the fluorescent compound is indicative of the presence of the sample polynucleotide and (2) one or more size standards, each of the size standards having a different mobility. Each of the size standards is typically essentially free or free of polynucleotides.

The fluorescent compound may be an intercalating compound, e.g., ethidium bromide or an acridine compound, that intercalates with the polynucleotide and exhibits enhanced fluorescence when so intercalated.

Migration coordinates of the sample polynucleotide and size standards are determined. The migration coordinate may be, e.g., a migration time, migration distance, or a migration coordinate determined from a combination thereof, such as a mobility. A size of the sample polynucleotide is determined using the migration coordinates of the sample polynucleotide and the migration coordinates of the size standards.

A size standard that is essentially free of polynucleotides lacks polynucleotide sequences longer than about 10 bases and/or base pairs. In some embodiments, the size standards lack polynucleotide sequences longer than about 5 bases and/or base pairs. A size standard that is free of polynucleotides even lacks polynucleotide sequences having two adjacent nucleotides or derivatives of nucleotides.

In some embodiments, the size standards are essentially free of nucleic acids, nucleotides and/or nucleosides. Exemplary size standards comprise less than about 10%, less than about 5%, less than about 2.5%, less than about 1%, e.g., less than about 0.5% by mass of nucleic acids, nucleotides and/or nucleosides (combined weight if a combination is present).

In some embodiments, the size standards comprise less than about 10%, less than about 5%, less than about 2.5%, less than about 1%, e.g., less than about 0.5% by mass of nucleic acids. In some embodiments, the size standards are free of nucleic acids.

In some embodiments, the size standards comprise less than about 10%, less than about 5%, less than about 2.5%, less than about 1%, e.g., less than about 0.5% by mass purine, pyrimidine, and derivatives of these compounds, e.g., thiamine, uracil, cytosine, adenine, and guanine. The size standards may be free of purine and pyrimidine and derivatives of these compounds. The size standards may be free of any, all, or some combination of thiamine, uracil, cytosine, adenine, and guanine.

In some embodiments, the size standards, even when in the presence of sample polynucleotides to be analyzed, are free of double stranded polynucleotides, e.g., such size standards typically do not form duplex regions with single stranded polynucleotides even at temperatures between about 15° C. and about 35° C.

Subjecting the sample polynucleotide to electrophoresis preferably comprises irradiating the intercalating compound with light and detecting, at a first wavelength, fluorescent light indicative of the presence of the sample polynucleotides. Subjecting the size standards to electrophoresis preferably comprises irradiating the size standards with light and detecting, at a second, different wavelength, fluorescent light indicative of the presence of the size standards. The first and second wavelengths are generally sufficiently different that the sample polynucleotide and size standards can be detected in the presence of one another without substantial interference.

Fluorescent light associated with the intercalating compound is generally not indicative of the presence of the size standards because the size standards are generally essentially free or totally free of intercalated intercalating compound, e.g., the intercalating compound either does not intercalate with or otherwise associate with the size standards or does not exhibit increased fluorescence when intercalated with or otherwise associated with the size standard. If the intercalating compound does associate with the size standards, the fluorescence of the intercalating compound when so associated is substantially lower than when intercalated with the sample polynucleotides. Thus, certain size standards may be said to be immune to the intercalating dye.

Detecting light at the second, different wavelength may comprise preventing at least some light at the first wavelength from reaching a detector or portion thereof. For example, a grating, prism, or optical filter may be placed along an optical path between the size standards and the detector to allow light having the second wavelength to reach the detector but to substantially prevent light having the first wavelength from reaching the same portion of the detector as the second wavelength. Thus, if a two dimensional detector is used, first light indicative of the presence of the sample polynucleotides may reach a first portion of the detector and second light indicative of the presence of the size standards may reach a second different portion of the detector.

The sample polynucleotides and size standards may be subjected to electrophoresis simultaneously along the same separation lane, such as within the same capillary.

The polynucleotides and size standards may be subjected to electrophoresis in the presence of a buffer.

In some embodiments, the size standards have a net charge in the buffer. These size standards can be used, e.g., in the presence of electroosmotic flow.

The mass to charge ratio of size standards in accordance with the present invention may be varied to achieve different mobilities. Thus, size standards of the present invention may have similar sizes and/or masses to one another but different charges that result in different mobilities. Exemplary size standards having variable mass to charge ratios include e-Tag reporters available from Aclara Incorporated.

The mobility of a given size standard may different from a mobility of a sample polynucleotide having the same mass. Determining a size of the sample polynucleotide may comprise using a relationship between the mobility of each size standard and the mobility of a reference polynucleotide having a known size and/or mass. Such a relationship may be determined using, for example, calibration data including (1) data indicative of a mobility of the size standards as a function of masses or other physical parameter thereof and (2) data indicative of a mobility of reference polynucleotides as a function of their mass or other physical parameters. Based on such calibration data one may determine the mass or other physical parameter of a sample polynucleotide based on a determination of the mobilities of the sample polynucleotide and the size standards.

The mobility of each size standard may be different from a mobility of a sample polynucleotide having the same size and determining a size of the sample polynucleotide may comprise using a predetermined relationship between the mobility of each size standard and the mobility of a polynucleotide having the same size.

The mobility of each size standard may be different from a mobility of a sample polynucleotide having the same length and determining a size of the sample polynucleotide may comprise using a predetermined relationship between the mobility of each size standard and the mobility of a polynucleotide having the same length.

Another aspect of the invention relates to a method of determining a relationship between the mobility of a plurality of size standards and a mobility of at least one reference polynucleotide, wherein the relationship between the mobilities of the size standards and the reference polynucleotide may be used in a method for electrophoretically determining a size of a sample polynucleotide. The method comprises providing a plurality of size standards, each of the size standards having a different mobility and each of the size standards generally being at least essentially free of polynucleotides. A plurality of reference polynucleotides is provided. Each of the reference polynucleotides preferably has a different size.

The size standards and the reference polynucleotides are subjected to electrophoresis. Migration coordinates of the size standards and reference polynucleotides are determined. A relationship between mobilities of the size standards and the mobilities of the reference polynucleotides is determined, whereby the size of a sample polynucleotide may be determined by (1) subjecting the sample polynucleotide to electrophoresis in the presence of size standards to determine migration coordinates of the size standards and sample polynucleotides and (2) using at least the migration coordinates of the size standards and sample polynucleotides and the determined relationship between the mobilities of the size standards and the reference polynucleotides.

Yet another aspect of the invention relates to a computer-readable medium comprising executable software code, the code for processing electrophoresis data to determine a size of at least one sample polynucleotide, the electrophoresis data comprising (1) peaks indicative of a separation of at least one sample polynucleotide along a first separation lane and (2) peaks indicative of a separation of a plurality of size standards along the first separation lane, the size standards being essentially free of polynucleotides, the computer-readable medium comprising:

code to determine a migration coordinate of at least one peak corresponding to the presence of the sample polynucleotide subjected to electrophoresis along the first separation lane;

code to determine migration coordinates of peaks indicative of a presence of at least two size standards subjected to electrophoresis along the first separation lane; and code to determine the size of the sample polynucleotide based on at least mobilities of the size standards and mobilities of reference polynucleotide having known sizes.

An additional aspect of the invention relates to a method of determining a size of a sample polynucleotide. A sample polynucleotide is subjected to electrophoresis in the presence of at least (1) an intercalating dye having a first fluorescent spectrum, wherein detection of light of the first fluorescence spectrum is indicative of the presence of the sample polynucleotide and (2) a plurality of size standards, each of the size standards having a different mobility and wherein detection of the light of the first fluorescence spectrum is essentially not indicative of a presence of the size standards. The presence of the size standards is preferably determined by detecting light having a wavelength different from the light of the first fluorescence spectrum detected to determine the presence of the sample polynucleotides.

A migration coordinate of the sample polynucleotide is determined. A migration coordinate of the each size standard is determined. A size of the sample polynucleotide is determined using the migration coordinate of the sample polynucleotide and the migration coordinates of the size standards.

Yet another aspect of the invention relates to a method of determining a size of a sample polynucleotide, comprising subjecting the sample polynucleotide to electrophoresis in the presence of at least (1) a fluorescent compound having a first fluorescence spectrum, wherein detection of light of the first fluorescence spectrum is indicative of the presence of the sample polynucleotide and (2) a plurality of non-polynucleotide size standards, each of the non-polynucleotide size standards having a different mobility.

A migration coordinate of the sample polynucleotide is determined. A migration coordinate of each of the plurality of non-polynucleotide size standards is determined. A size of the sample polynucleotide is determined using the migration coordinate of the sample polynucleotide and the migration coordinates of the non-polynucleotide size standards.

A non-polynucleotide size standard is a compound which resists intercalation by ethidium bromide. For example, one such compound is essentially free of double stranded polynucleotides. A preferred non-polynucleotide size standard is a linear polymer that is at least essentially free of nucleic acids or nucleotides.

Size standards may be used to determine whether the introduction of a sample to an electrophoresis lane was successful, which determination can otherwise be difficult, e.g., if no detectable sample component was introduced as in a negative control samples.

Standards may be used to calibrate migration coordinates, such as to correct for capillary-to-capillary variation in migration times.

Standards may be used as a size stamp, such as to determine a size of DNA fragments or other polynucleotides.

Typically, a plurality of standards are used. In some embodiments, the migration velocity difference between successive standards is the same. In other embodiments, the migration velocity difference between successive standards increases or decreases with the average migration velocity of the successive standards.

In some embodiments, the size standards are essentially free or free of amino acids including an amino group and/or amino acids including a sulfur atom, advantageously reducing a tendency of the size standards to interact with the walls, e.g., the inner capillary wall, of a separation lane.

In some embodiments, the size standards are free of amino acids having pendant primary amines, secondary, or tertiary amines, e.g., the size standards may be free of one or more of the amino acids lysine, glycine, arginine, asparagines, or histidine, and tryptophan. In some embodiments, the size standards are free of amino acids having sulfur groups, e.g., the size standards may be free of one or more of the amino acids methionine or cysteine.

DETAILED DESCRIPTION OF THE PRESENT INVENTION

Figure 1:
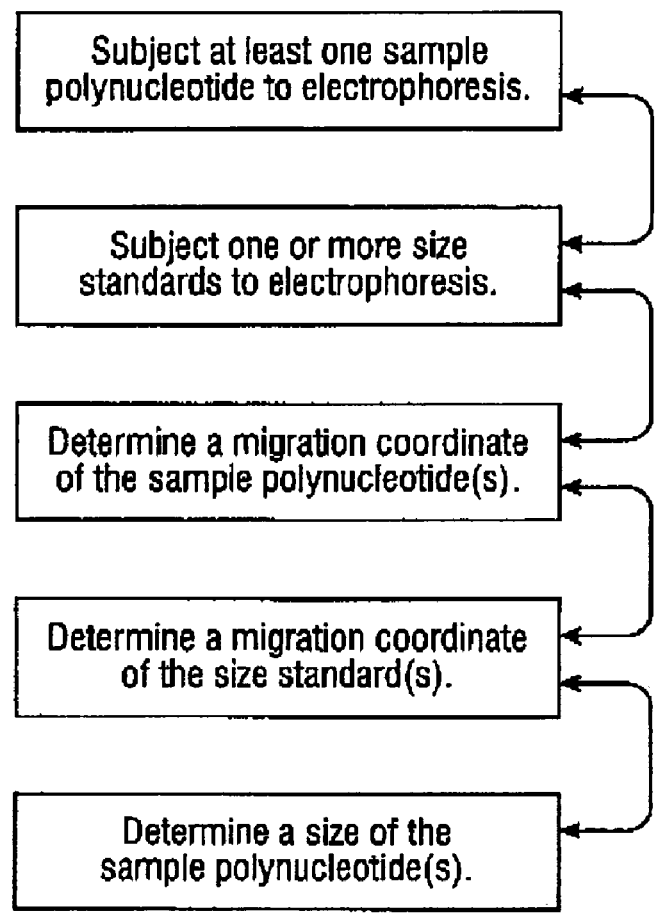
FIG. 1 shows a flow chart of a method of the present invention.

Referring to the flow chart of FIG. 1, a method of determining a size of one or more sample polynucleotides includes subjecting one or more sample polynucleotides to electrophoresis along an electrophoresis lane, subjecting one or more size standards to electrophoresis, determining a migration coordinate of the one or more sample polynucleotides, determining a migration coordinate of the one or more size standards, and determining a size, e.g., a length, of at least one of the one or more sample polynucleotides.

The sample polynucleotides may include, e.g., single stranded polynucleotides, double stranded polynucleotides, or a combination thereof. The polynucleotides may comprise, e.g., RNA, DNA, or combination thereof.

Exemplary electrophoresis lanes include a bore of a capillary, an electrophoresis lane of a microfabricated microfluidic device, or a lane within a slab gel.

The one or more sample polynucleotides are typically subjected to electrophoresis in the presence of at least one fluorescent compound having a first fluorescent spectrum, wherein detection of light of the first fluorescence spectrum is indicative of the presence of the one or more sample polynucleotides.

The fluorescent compound can be an intercalating dye, e.g., ethidium bromide, having a fluorescence indicative of the presence of double stranded polynucleotides.

The fluorescent compound can be a tag, covalently bound to a portion of the sample polynucleotide.

In some embodiments, e.g., where a mixture of more than one sample polynucleotide is subjected to electrophoresis, different fluorescent compounds can be used. For example, fluorescent compounds having different fluorescent spectra and indicative of different bases of the polynucleotides can be used. An exemplary mixture includes a plurality of polynucleotide fragments having different lengths.

The one or more size standards are generally subjected to electrophoresis along the same electrophoresis lane as the one or more sample polynucleotides and in the presence thereof. For example, a mixture including the size standard(s) and the sample polynucleotide(s) can be subjected to electrophoresis along an electrophoresis lane, e.g., a capillary.

Each of the size standards typically has a different mobility so that the size standards exhibit a plurality of different migration times when subjected to electrophoresis. A plurality of size standards exhibiting different migration times can be referred to as a ladder. A difference $\Delta tm$ in the migration time of successive size standards can be constant among the standards or may vary among different pairs of successive standards.

In some embodiments, the size standards are at least essentially free or free of one or more of double stranded polynucleotides, single stranded polynucleotides, all polynucleotides, nucleotides, nucleosides, nucleic acids, purine (and/or derivatives thereof), or pyrimidine (and/or derivatives thereof).

In some embodiments, the ratio of the mass of double stranded polynucleotides of the size standard to the total mass of a size standard is less than about 10%, less than about 5%, less than about 2.5%, less than about 1%, e.g., less than about 0.5%.

In some embodiments, the ratio of the mass of single stranded polynucleotides of the size standard to the total mass of a size standard is less than about 10%, less than about 5%, less than about 2.5%, less than about 1%, e.g., less than about 0.5%.

In some embodiments, the ratio of the mass of all polynucleotides of the size standard to the total mass of a size standard is less than about 10%, less than about 5%, less than about 2.5%, less than about 1%, e.g., less than about 0.5%.

In some embodiments, the ratio of the mass of nucleotides of the size standard to the total mass of a size standard is less than about 10%, less than about 5%, less than about 2.5%, less than about 1%, e.g., less than about 0.5%.

In some embodiments, the ratio of the mass of nucleosides of the size standard to the total mass of a size standard is less than about 10%, less than about 5%, less than about 2.5%, less than about 1%, e.g., less than about 0.5%.

In some embodiments, the ratio of the mass of nucleic acids of the size standard to the total mass of a size standard is less than about 10%, less than about 5%, less than about 2.5%, less than about 1%, e.g., less than about 0.5%.

In some embodiments, the ratio of the mass of purine (and/or derivatives thereof) of the size standard to the total mass of a size standard is less than about 10%, less than about 5%, less than about 2.5%, less than about 1%, e.g., less than about 0.5%.

In some embodiments, the ratio of the mass of pyrimidine (and/or derivatives thereof) of the size standard to the total mass of a size standard is less than about 10%, less than about 5%, less than about 2.5%, less than about 1%, e.g., less than about 0.5%.

The size standards may be polymers or other compounds in which a structure repeats. In some embodiments, the size standards are linear polymers or branched polymers.

Exemplary size standards have a narrow molecular weight distribution (low polydispersity).

In some embodiments, the size standards include at least one of oligosaccharides or polysaccharides, such as carbohydrates, dextrans, poly-dextrans, starches, and pullulins. The oligosaccharides or polysaccharides may be labeled with fluorescent dyes including, e.g., 8-Amino-1,3,6-pyrenetrisulfonic acid (ATTS) (Morell et al. 1998. Electrophoresis 19, 2603-2611.). DTAF can be used as a tag.

Other size standards include Polystyrene sulfonate, Polyethylene oxide, e.g., tagged with DTAF, fluorescein derivatives such as fluorescein mercuric acetate, and amphotericin-B+FQ.

In some embodiments, the size standards include one or more peptoids (e.g., a polyamide having one or more substituent on the amide nitrogen atom). Typical peptoids are synthetic analogs of peptides different in that while a side-chain residue on a peptide is attached to a carbon atom alpha to the carbonyl group, in a peptoid the "side-chain residue", is attached to the amide nitrogen atom. An exemplary "polypeptoid" is a poly-(N-substituted glycine) compound.

Referring to TABLE I, a size standard, in some embodiments, includes a plurality of amino acids, e.g. the size standards include or are peptides.

In some embodiments, the size standards are essentially free or free of amino acids having an amino group. By essentially free it is meant that fewer than 10% of amino acids of the size standard have an amino group.

In some embodiments, the size standards are essentially free or free of amino acids having a sulfur atom. By essentially free it is meant that fewer than 10% of amino acids of the size standard have a sulfur atom.

A terminal amino acid of peptide size standards typically contains a COO— group in basic solution. Basic is defined as a solution having a pH greater than 7, e.g., between pH 9 and pH 11.

A fluorescent tag, e.g., FITC, is bound to the peptide, e.g., by covalent bonding to the amino acid at position 1 such as to the N-terminus thereof. FITC is understood to have a negative charge in basic solution. The tag-size standard bond may be at the C-terminus. In such embodiments, the COO— moiety may be removed and a group with a negative charge may be added or present on the standard, e.g., the standard may have a glutamic acid residue.

TABLE I

Exemplary Peptide Size Standards.

| Size Standard | TAG | SEQ ID NO: | Position | | | | | | | | | | | | EST. | | |
|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | MW | CHG. | M/Z |
| 01 | FITC | 1 | Tyr | Val | Ala | Asp | OH | | | | | | | | 856 | −2 | 428 |
| 02 | FITC | 2 | Tyr | Val | Ala | Asp | Ala | Pro | Lys | Dnp | OH | | | | 1318 | −4 | 330 |
| 03 | FITC | 3 | Thr | Thr | Thr | Thr | Thr | Thr | Thr | Thr | Thr | Thr | Thr | Thr | 1429 | −2 | 715 |
| 04 | FITC | 4 | Thr | Thr | Thr | Thr | Thr | Thr | Thr | Thr | Thr | Thr | | | 1191 | −2 | 596 |
| 05 | FITC | 5 | Thr | Thr | Thr | Thr | Thr | Thr | Thr | Thr | | | | | 953 | −2 | 477 |
| 06 | FITC | 6 | Thr | Thr | Thr | Thr | Thr | Thr | | | | | | | 715 | −2 | 358 |
| 07 | FITC | 3 | Thr | Thr | Thr | Thr | Thr | Thr | Thr | Thr | Thr | Thr | Thr | Thr | 1429 | −2 | 715 |
| 08 | FITC | 7 | Thr | Thr | Thr | Thr | Thr | Thr | Thr | Thr | Thr | Thr | Thr | Glu | 1448 | −3 | 483 |
| 09 | FITC | 8 | Thr | Thr | Thr | Thr | Glu | Thr | Thr | Thr | Thr | Thr | Thr | Glu | 1467 | −4 | 367 |
| 10 | FITC | 9 | Thr | Thr | Thr | Glu | Thr | Thr | Thr | Glu | Thr | Thr | Thr | Glu | 1486 | −5 | 297 |
| 11 | FITC | 10 | Thr | Leu | Thr | Thr | Thr | Leu | Thr | Thr | Thr | Leu | Thr | Thr | 1465 | −2 | 733 |
| 12 | FITC | 11 | Thr | Leu | Thr | Thr | Thr | Leu | Thr | Thr | Thr | Leu | Thr | Glu | 1484 | −3 | 495 |
| 13 | FITC | 12 | Thr | Leu | Thr | Thr | Glu | Leu | Thr | Thr | Thr | Leu | Thr | Glu | 1503 | −4 | 371 |
| 14 | FITC | 13 | Thr | Leu | Thr | Glu | Thr | Leu | Thr | Glu | Thr | Leu | Thr | Glu | 1522 | −5 | 304 |

In some embodiments, the size standards are proteins, i.e., size standards having 50 or more amino acids. The size standards may be polypeptides, e.g., peptides having fewer than 50 amino acids or fewer than 25 amino acids. The size standards may be oligopeptides, e.g., peptides having fewer than 15 amino acids or about 12 or fewer amino acids. The size standards generally have masses of fewer than 10 kilo Daltons, 5 kilo Daltons, 2.5 kilo Daltons, 2.0 kilo Daltons, or 1.5 kilo daltons.

The size standards may include linear chains of amino acids (as opposed to branched chains or in combination therewith).

In TABLE I, the identities of amino acids at various positions along linear peptides are shown. The various amino acids are Thr=threonine, Val=valine, Ala=alanine, Asp=aspartic acid, Pro=proline, Dnp=dinitrophenyl group, Lys=lysine, Glu=glutamic acid, and Leu=leucine. Derivatives of these amino acids, other amino acids and/or their derivatives may also be used. Exemplary size standards include FITC(Tyr)(Val)(Ala)(Asp)(Ala)(Pro)(Lys)(Dnp)OH (SEQ ID NO:2), (Thr)10+FQ or CBQ (SEQ ID NO:14), (Thr)4Glu(Thr)5+FQ or CBQ (SEQ ID NO:15), and FITC (Thr)(Leu)(Thr)(Thr)(Thr)(Leu)(Thr)(Thr)(Thr)(Leu)(Thr) (Thr)OH (SEQ ID NO:10).

Fluorescent tags other than FITC may also be used.

Various standards of TABLE I have migration times that are generally similar to polynucleotides having lengths of about 100 base pairs to about 600 base pairs.

Standards 1 and 2 of TABLE I can be obtained as respective part numbers M-2280 and M-2285, from BACHEM, Bioscience, Inc., King of Prussia, Pa., 19406, USA. Other standards of TABLE I can be synthesized using known synthetic techniques.

The molecular weight (MW), estimated charge, and estimated mass to charge ratio (M/Z) in basic solution of each size standard is shown. The mass and charge include any mass and charge of the FITC.

In some embodiments, a respective mass of size standards of a plurality of size standards differs because the size standards have increasing numbers of a particular amino acid, which may be a substantially neutral amino acid at a pH between 7 and 11. Standards 3-6 of TABLE I have different numbers of the amino acid threonine.

In some embodiments, a respective M/Z of size standards of a plurality of size standards differs but the mass of the size standards varies by less than 5%, less than 2.5%, or less than 1%. Standards 7-10 of TABLE I are examples of such size standards.

In some embodiments, the polarities and/or solubilities of size standards of a plurality of size standards are modified by the introduction of different numbers of substantially polar or non-polar (Leu) amino acids to the size standards. Enhancing the solubility can assist clean-up of synthesized standards (as by liquid chromatography). Other suitable size standards include protein conjugates, which may be labeled with fluorescent dyes, e.g., succinimidyl ester derivatives such as the available from Molecular Probes.

Yet more suitable size standards include beads of varying size or charge to mass ratio that exhibit different mobilities when subjected to electrophoresis. The beads may be tagged with a fluorophore to facilitate their detection.

Typical size standards do not substantially modify the electrophoretic mobility of the sample polynucleotide(s) even when subjected to simultaneous electrophoresis in a mixture therewith. In some embodiments, the size standard is chemically inert with respect to the polynucleotide or at least resistant to interaction with the sample polynucleotide. For example, the size standard and sample polynucleotide may have a low affinity so as to resist binding to one another or otherwise forming a complex therewith.

In some embodiments, the migration time difference $\Delta tm$ between successive standards is substantially independent of the physical and chemical environment within the electrophoresis lane, e.g., the pH, temperature, voltage and other compounds employed in the separation (buffers, denaturants, sieving matrices, etc.). In some cases, the migration time difference $\Delta tm$ depends on the physical and chemical environment but changes uniformly between successive standards. For example, the change in $\Delta tm$ between different size standards may be proportional to the average migration time of the successive standards.

Size standards typically do not adhere to the inner surface of the electrophoresis lane, e.g., the inner wall of a capillary, to a degree sufficient to substantially broaden peaks indicative of the presence of the size standards.

Size standards generally produce peaks that are uniform between successive runs within a capillary (absent changed migration conditions within the capillary). Size standards generally produce peaks that are uniform between different capillaries of multi-capillary systems, assuming uniform migration conditions between different capillaries.

Size standards generally resist degradation, polymerization, precipitation or other processes that might alter the migration time difference $\Delta tm$ between successive standards.

In some embodiments, the size standards have a net charge. In some embodiments, the net charge of each size standard is substantially independent of pH for variations of fewer than 6 pH units, fewer than 3 pH units, e.g., fewer than 1.5 pH units. In some embodiments, the size standards do not have a plurality of acidic groups or protons having different pKa's.

In some embodiments, a peak produced by detection of a given size standard has a full width half maximum (FWHM) equivalent to a fewer than 10 base difference, a fewer than 7 base difference, a fewer than 5 base difference, a fewer than 3 base difference, e.g., a 2 base difference or fewer, as compared to a polynucleotide having a similar migration time. Here the base differences are in length. For example, consider a polynucleotide (whether a single stranded or double stranded polynucleotide) having a length of 75 bases. A peak produced by detection of a size standard having a peak width equivalent to a fewer than 7 base difference with respect to this polynucleotide and having a migration time about equal to the polynucleotide would yield a peak having a FWHM narrower than the difference in migration time between the 75 base polynucleotide and an otherwise identical polynucleotide having 7 additional bases.

The presence of the size standards can generally be determined directly, e.g., via fluorescence or absorbance of the size standards themselves. In some embodiments, the size standards can be detected via a tagging agent, e.g., a covalently bound fluorophore. A plurality of different tagging agents may be used for different size standards. Exemplary tagging agents include FITC, CBQ, e.g., for tagging tertiary amines of peptide size standards, and DTAF, e.g., for tagging pendant OH groups on polysaccharides. In general, different size standards are tagged with the same number of tagging agents, e.g., one tagging agent per size standard, to reduce peak broadening of the size standards.

The size standard can generally be distinguished spectroscopically from the tag (or intercalating dye) indicative of the sample polynucleotide(s). For example, the size standard or associated tag may emit fluorescence, have a fluorescence excitation spectrum, and/or absorb light at a different wavelength than the tag (or intercalating dye) indicative of the sample polynucleotide(s). Thus, even if a size standard and a sample polynucleotide co-elute with one another, the presence of both can generally be determined. For example, an FITC tagged size standard and a double-stranded polynucleotide with intercalated ethidium bromide may be detected and discriminated even when present together because the size standard tag (FITC) and the intercalating dye (ethidium bromide) have different fluorescence spectra.

In some embodiments, the size standards do not interact with intercalating dyes to increase the fluorescence thereof. For example, the fluorescence of intercalating agents, e.g., ethidium bromide, increases in the presence of double stranded DNA when intercalated therewith. Typical size standards can be subjected to electrophoresis in the presence of intercalating agents, e.g., ethidium bromide, without substantially increasing the fluorescence of the intercalating agent as compared to the agent in free solution.

Upon subjecting the sample polynucleotide(s) and size standard(s) to electrophoresis, electrophoresis data is obtained. Exemplary electrophoresis data include fluorescence intensity versus time data. Migration coordinates, such as migration times, of the sample polynucleotide and size standards are determined from the electrophoresis data.

A size of the sample polynucleotide is determined using the migration coordinate(s) of the sample polynucleotide(s) and the migration coordinate(s) of the size standard(s). It should be understood that the size standard(s) may be subjected to electrophoresis before or after the sample polynucleotide(s).

In some embodiments, migration coordinates of size standards are determined prior to subjecting the sample polynucleotides to electrophoresis. The size standard migration coordinate data is saved, for example using a computer readable medium. Upon obtaining electrophoresis data of the sample polynucleotide(s), the sizes thereof are determined using the previously acquired migration coordinate data of the size standard(s).

Electrophoresis may be performed using electrophoretic separation lanes known in the art. Exemplary separation lanes include the internal bores capillaries filed with a sieving matrix that causes polynucleotides of varying sizes to migrate with different velocities. An exemplary instrument for performing capillary electrophoresis is disclosed in U.S. Pat. No. 6,027,627, which patent discloses an automated parallel electrophoretic system. The patent is incorporated by reference herein.

Figure 2:
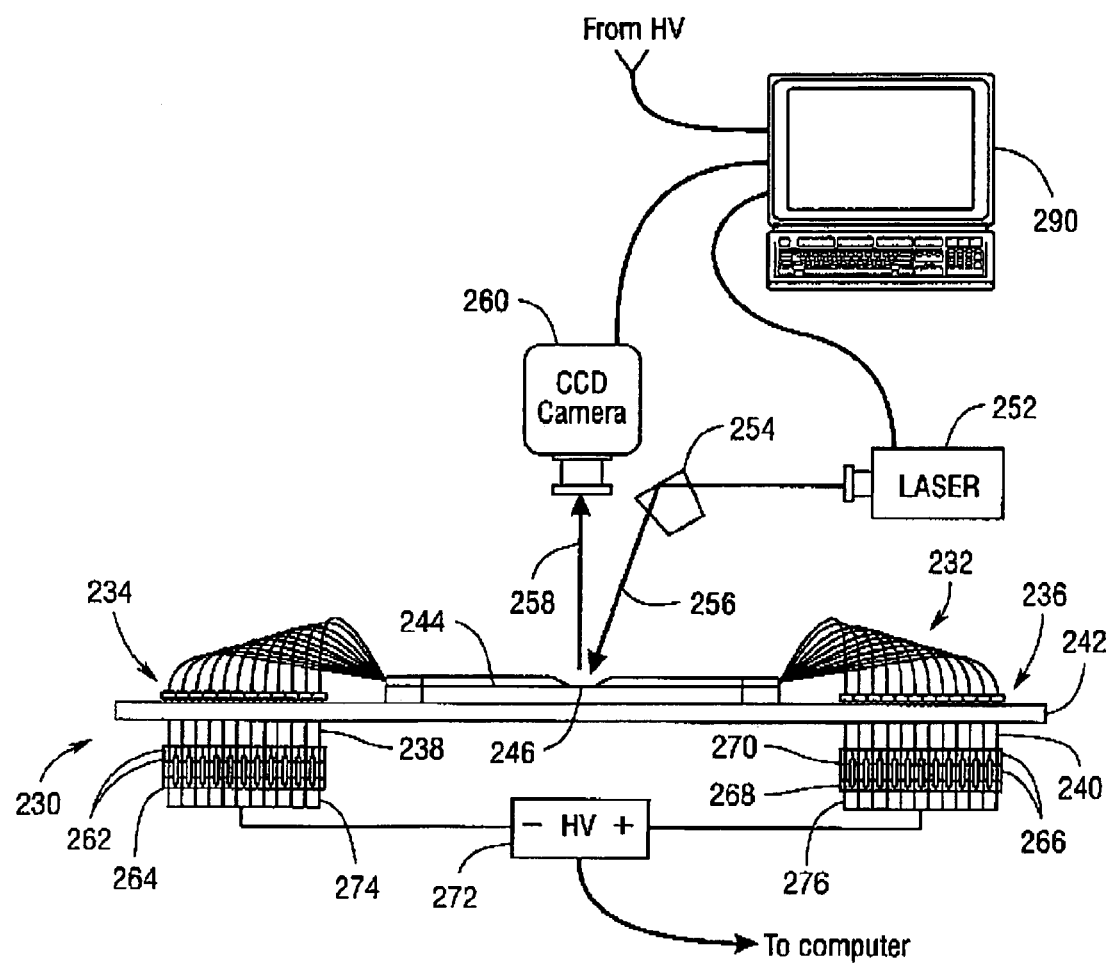
FIG. 2 shows an electrophoresis system.

Referring to FIG. 2, an electrophoresis system 230 in accordance with the present invention includes a plurality of capillaries 232. A first array of ends 238 of the capillaries 232 may be spaced apart in substantially the same manner as the wells 262 of a microtitre tray 264. This allows one to simultaneously perform capillary electrophoresis on volumes of material present in respective wells 262 of the tray 264. Thus, one or more size standards and sample polynucleotide(s) may be placed in various wells of the tray. The array of capillary ends 238 is placed in contact with the volumes of material in the wells 262. Upon the brief application of a current through the capillaries, an amount of the material is drawn into the respective capillaries of the array. The current is provided by a source 272 of high-voltage (HV) electricity. The array of capillary ends 238 is placed in contact with a solution of buffer. Upon the renewed application of an electric field to the capillaries 232, compounds previously drawn into the capillaries 232 from the wells 262 migrate toward a detection zone 246.

A detection zone 246 is spaced apart from the array of capillary ends 238 along a separation axis of capillaries 232. A detection system determines the presence of compounds in the detection zone. Exemplary detection systems include a light source 252 and a detector 260. Compounds present in the detection zone are irradiated with light 256 from the light source 252. A beam steering element 254 may be used to direct light 256 toward the detection zone. The irradiated compounds or fluorophores associated with the compounds may emit fluorescence 258.

Electrophoresis data typically includes one or more subsets of data defining peaks, which are indicative of the presence of a sample polynucleotide or a size standard subjected to electrophoresis. A migration coordinate of a peak, such as a migration time $\tau_p$ of the peak, may be determined by fitting the peak to a peak-shape model and determining the peak migration coordinate from the parameters of the fitted peak. Alternatively, one may simply determine a peak migration time from a peak maximum of the observed migration time data.

A computer 290 includes a computer-readable medium comprising code that when executed receives the detector signal from detector 260 and process the data in accordance with the invention. The code is discussed elsewhere herein.

The electrophoresis system of the invention may include a computer or other processor configured to determine a size of one or more sample polynucleotides. The processor is typically implemented through a combination of hardware and executable software code. In the usual case, the processor includes a programmable computer, perhaps implemented as a reduced instruction set (RISC) computer, which handles only a handful of specific tasks. The computer is typically provided with at least one computer-readable medium, such as a PROM, flash, or other non-volatile memory to store firmware and executable software code, and will usually also have an associated RAM or other volatile memory to provide work space for data and additional software. Various steps that may be carried out by the computer or other processor in response to code of the computer-readable medium are discussed below.

The computer or processor may be configured to receive a detector signal. Because the computer may be either local to the electrophoresis instrument or remote therefrom, the computer may receive the detector signal through, for example, a hardwired connection, wireless connection, a network, a storage medium such as a disk, or combination thereof.

The code of the computer readable medium may, optionally, include code configured to convert the detector signal to electrophoresis data. Because the detector may output a detector signal in the form of electrophoresis data including a detector coordinate, such as an intensity, and a migration coordinate, such as a time, a conversion step may not be necessary.

In certain situations, the raw data must be subjected to initial conditioning 304, such as by data smoothing, baseline subtraction, or by using deconvolution techniques to identify overlapped peaks. Suitable data conditioning techniques, such as those discussed below, are disclosed in U.S. application Ser. No. 09/676,526, filed Oct. 2, 2000, titled Electrophoretic Analysis System Having in-situ Calibration, which application is hereby incorporated to the extent necessary to understand the present invention. The computer-readable medium includes code to perform such conditioning.

Smoothing can be accomplished by using, for example, a Savitzky-Golay convoluting filter to improve the signal to noise ratio. Optimal properties of the filter, such as the width and order, can be determined by a user of the present invention on the basis of the signal to noise ratio of the data and the widths of peaks in the data.

Baseline subtraction can be performed to eliminate baseline drift. Typically, minima are identified in successive local sections of data, e.g., every 300 data points. Two or more minima in adjacent sections are connected, such as by a straight line or a polynomial fit to the minima. The values along the line connecting the minima are then subtracted from the intervening raw data. The new values after the baseline subtraction and smoothing are stored for further processing. The order of data smoothing and baseline subtraction can be reversed.

Overlapped peaks within the separations data can be identified and resolved using peak-fitting techniques. In most electrophoresis separations, the earlier-detected peaks are narrower than the later-detected, slower moving peaks. Within a given local section of data, however, peaks due to the presence of a single fragment have similar widths. Moreover, adjacent peaks rarely overlap exactly. Rather, the overlapped peaks a generally offset from one another. Accordingly, peaks due to the presence of multiple fragments tend to be wider than the single fragment peaks. Once a region of data containing overlapped peaks is identified, the underlying peaks can be resolved by fitting a model of the data to the observed data. Typically, the peak fitting model includes parameters that describe the amplitude, position, and width of each underlying peak.

The code may also be configured to determine (1) a migration coordinate of at least one peak corresponding to the presence of the sample polynucleotide subjected to electrophoresis along the first separation lane and (2) migration coordinates of at least two peaks respectively indicative of the presence of least two size standards subjected to electrophoresis along the first separation lane.

The code may be configured to determine the size of the sample polynucleotide based on at least a relationship between the mobility of the size standard(s) and the mobility of one or more reference polynucleotides having known sizes.

Detector 260 is typically a two dimensional imaging detector, e.g., a CCD having a plurality of pixels arranged in rows and columns. Detection zones of different capillaries are imaged upon different positions of the detector. In some embodiments, light from the detection zones is wavelength-dispersed so that at least two images of each detection zone reach the detector. A first position of the detector receives light having a first wavelength or wavelength range and a second position of the detector receives light having a second, different wavelength or wavelength range. For example, the first wavelength or range may correspond to fluorescence from an intercalating dye, e.g., ethidium bromide, and the second wavelength or range may correspond to fluorescence from a size standard, e.g., an FITC tag thereof.

In the absence of cross talk, a given position of the detector will receive light from the detection zone of only a single capillary. In general, however, cross talk occurs so that at least some light arising from the detection zone of a given capillary reaches a detector position corresponding to the detection zone of another capillary, typically an adjacent capillary. Because the intercalating dye is generally continually present in all capillaries of the array and fluoresces to some extent even when not intercalated, it can be difficult to determine the extent of cross talk between capillaries.

In some embodiments of the invention, a fluorescent compound having a wavelength different from the intercalating dye is added to at least some of the capillaries. Typically, the fluorescent compound is immune to the intercalating dye. The fluorescent compound, which may be a size standard as discussed herein, migrates along the capillaries and reaches the detection zone thereof but is not simultaneously present in the detection zone of at least one other capillary, e.g., one or both adjacent capillaries. This can be accomplished by only introducing the fluorescent compound into some, but not all capillaries, introducing the fluorescent compound into different capillaries at different times, or introducing fluorescent compounds having different mobilities into different capillaries so that the compounds reach the detection zones at different times.

Light from the fluorescent compound present in the detection zone of one or more different capillaries is imaged onto the detector. At least some light from fluorescent compound present in the detection zone of a given capillary may reach the detector at a position corresponding to the detection zone of a different capillary in which the fluorescent compound is known not to be simultaneously present. The amount of light reaching the detector at the position corresponding to the other capillary is indicative of the amount of cross talk between the two capillaries. A similar analysis can be performed between any combination of capillaries of the array to determine the amount of cross talk.

The extent of cross talk can be used to correct fluorescence signals received from a capillary to account for light that actually arose from the detection zones of one or more other capillaries.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

---

What is claimed is:

1. A method of determining a size of a sample polynucleotide, comprising:
   subjecting a sample polynucleotide to electrophoresis in the presence of at least:
      a fluorescent intercalating compound having a first fluorescence spectrum, wherein detection of light of the first fluorescence spectrum is indicative of the presence of the sample polynucleotide, a size standard having a net charge in solution, the size standard being essentially free of polynucleotides;
   determining a migration coordinate of the sample polynucleotide;
   determining a migration coordinate of the size standard; and
   determining a size of the sample polynucleotide using the migration coordinate of the sample polynucleotide and the migration coordinate of the size standard.

2. The method of claim 1, wherein:
   the step of subjecting comprises subjecting the sample polynucleotide to electrophoresis in the presence of a plurality of size standards, each of the size standards having a different mobility and wherein each of the size standards is essentially free of polynucleotides; and
   the method comprises determining the migration coordinates of each of the size standards.

3. The method of claim 2, wherein said plurality of size standards comprises at least two size standards, wherein said at least two size standards comprise at least one of an oligosaccharide, a polysaccharide, and a protein conjugate.

4. The method of claim 2, wherein a first size standard of said plurality of size standards is a polypeptide including a number of peptides and a second size standard is a different polypeptide having a different electrophoretic mobility.

5. The method of claim 4, wherein the first and second size standards have different numbers of peptides.

6. The method of claim 4, wherein the polypetides comprises a fluorescent tagging agent.

7. The method of claim 2, wherein the migration coordinates are migration times.

8. The method of claim 2, wherein the migration coordinates are electrokinetic mobilities.

9. The method of claim 2, wherein determining a migration coordinate of each of the plurality of size standards comprises detecting light having a wavelength of light different from a wavelength of light detected to determine the presence of the sample polynucleotide.

10. The method of claim 1, wherein the fluorescent compound having a first fluorescence spectrum is selected from intercalating dyes, groove binding dyes, other dyes that non-covalently associate with the polynucleotide, or any combination thereof.

11. A method of determining a size of a sample polynucleotide, comprising:
   subjecting the sample polynucleotide to electrophoresis in the presence of an intercalating compound;
   subjecting a size standard, having a net charge in solution, to electrophoresis, the size standard being essentially free of polynucleotides;
   detecting the presence of the intercalating compound to determine a migration coordinate of the sample polynucleotide;
   determining a migration coordinate of each of the plurality of size standard;
   determining a size of the sample polynucleotide using the migration coordinate of the sample polynucleotide and the migration coordinates of the size standard.

12. The method of claim 11, wherein:
   the step of subjecting the subjecting a size standard to electrophoresis comprises subjecting a plurality of size standards to electrophoresis, each of the size standards having a different mobility and each of the size standards being essentially free of polynucleotides; and
   the method comprises determining the migration coordinates of each of the size standards.

13. The method of claim 12, wherein said plurality of size standards comprises at least two size standards, wherein said at least two size standards comprise at least one of an oligosaccharide, a polysaccharide, and a protein conjugate.

14. The method of claim 12, wherein a first size standard of said plurality of size standards is a polypeptide including a number of peptides and a second size standard is a different polypeptide having a different electrophoretic mobility.

15. The method of claim 14, wherein the first and second size standards have different numbers of peptides.

16. The method of claim 14, wherein the polypetides comprises a fluorescent tagging agent.

17. The method of claim 14, wherein the steps of subjecting comprise separating the sample polynucleotide to electrophoresis in the presence of the size standards along the same separation lane.

18. The method of claim 11, wherein the migration coordinates are migration times.

* * * * *

SEQUENCE LISTING

<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Non naturally occurring peptide

<400> SEQUENCE: 1

Tyr Val Ala Asp
 1

<210> SEQ ID NO 2
<211> LENGTH: 7
<212> TYPE: PRT
<213> ORGANISM: Artificial Sequence
<220> FEATURE:
<223> OTHER INFORMATION: Non naturally occurring peptide

<400> SEQUENCE: 2

Tyr Val Ala Asp Ala Pro Lys
 1               5

<210> SEQ ID NO 3
<211> LENGTH: 12
<212> TYPE: PRT
<213> ORGANISM: Artificial Sequence
<220> FEATURE:
<223> OTHER INFORMATION: Non naturally occurring peptide

<400> SEQUENCE: 3

Thr Thr Thr Thr Thr Thr Thr Thr Thr Thr Thr Thr
 1               5                   10

```
<210> SEQ ID NO 4
<211> LENGTH: 10
<212> TYPE: PRT
<213> ORGANISM: Artificial Sequence
<220> FEATURE:
<223> OTHER INFORMATION: Non naturally occurring peptide

<400> SEQUENCE: 4

Thr Thr Thr Thr Thr Thr Thr Thr Thr Thr
 1               5                  10

<210> SEQ ID NO 5
<211> LENGTH: 8
<212> TYPE: PRT
<213> ORGANISM: Artificial Sequence
<220> FEATURE:
<223> OTHER INFORMATION: Non naturally occurring peptide

<400> SEQUENCE: 5

Thr Thr Thr Thr Thr Thr Thr Thr
 1               5

<210> SEQ ID NO 6
<211> LENGTH: 6
<212> TYPE: PRT
<213> ORGANISM: Artificial Sequence
<220> FEATURE:
<223> OTHER INFORMATION: Non naturally occurring peptide

<400> SEQUENCE: 6

Thr Thr Thr Thr Thr Thr
 1               5

<210> SEQ ID NO 7
<211> LENGTH: 12
<212> TYPE: PRT
<213> ORGANISM: Artificial Sequence
<220> FEATURE:
<223> OTHER INFORMATION: Non naturally occurring peptide

<400> SEQUENCE: 7

Thr Thr Thr Thr Thr Thr Thr Thr Thr Thr Thr Glu
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Non naturally occurring peptide

<400> SEQUENCE: 8

Thr Thr Thr Thr Glu Thr Thr Thr Thr Thr Thr Glu
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Non naturally occurring peptide

<400> SEQUENCE: 9

Thr Thr Thr Glu Thr Thr Thr Glu Thr Thr Thr Glu
 1               5                  10

<210> SEQ ID NO 10
```

```
<211> LENGTH: 12
<212> TYPE: PRT
<213> ORGANISM: Artificial Sequence
<220> FEATURE:
<223> OTHER INFORMATION: Non naturally occurring peptide

<400> SEQUENCE: 10

Thr Leu Thr Thr Thr Leu Thr Thr Thr Leu Thr Thr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Non naturally occurring peptide

<400> SEQUENCE: 11

Thr Leu Thr Thr Thr Leu Thr Thr Thr Leu Thr Glu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Non naturally occurring peptide

<400> SEQUENCE: 12

Thr Leu Thr Thr Glu Leu Thr Thr Thr Leu Thr Glu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Non naturally occurring peptide

<400> SEQUENCE: 13

Thr Leu Thr Glu Thr Leu Thr Glu Thr Leu Thr Glu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Non naturally occurring peptide
<220> FEATURE:
<221> NAME/KEY: VARIANT
<222> LOCATION: 11
<223> OTHER INFORMATION: xaa = Phe, Gln or Cys, Asx, Gln

<400> SEQUENCE: 14

Thr Thr Thr Thr Thr Thr Thr Thr Thr Thr Xaa
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Non naturally occurring peptide
<220> FEATURE:
<221> NAME/KEY: VARIANT
<222> LOCATION: 11
<223> OTHER INFORMATION: Xaa = Phe, Gln or Cys, Asx, Gln
```

-continued

```
<400> SEQUENCE: 15

Thr Thr Thr Thr Glu Thr Thr Thr Thr Xaa
1               5                   10
```